US009598581B2

(12) United States Patent
Robbins et al.

(10) Patent No.: US 9,598,581 B2
(45) Date of Patent: Mar. 21, 2017

(54) METHOD OF ISOLATING BLUE ANTHOCYANIN FRACTIONS

(71) Applicants: MARS, INCORPORATED, McLean, VA (US); THE OHIO STATE UNIVERSITY, Columbus, OH (US)

(72) Inventors: Rebecca J. Robbins, Hackettstown, NJ (US); J. Christopher Johnson, Turlock, CA (US); Thomas M. Collins, Hackettstown, NJ (US); Neda Ahmadiani, Columbus, OH (US); M. Monica Giusti, Dublin, OH (US)

(73) Assignees: MARS, INCORPORATED, McLean, VA (US); THE OHIO STATE UNIVERSITY, Columbus, OH (US)

( * ) Notice: Subject to any disclaimer, the term of this patent is extended or adjusted under 35 U.S.C. 154(b) by 0 days.

(21) Appl. No.: 14/773,103

(22) PCT Filed: Mar. 14, 2014

(86) PCT No.: PCT/US2014/027319
§ 371 (c)(1),
(2) Date: Sep. 4, 2015

(87) PCT Pub. No.: WO2014/152417
PCT Pub. Date: Sep. 25, 2014

(65) Prior Publication Data
US 2016/0017150 A1 Jan. 21, 2016

Related U.S. Application Data

(60) Provisional application No. 61/790,842, filed on Mar. 15, 2013.

(51) Int. Cl.
*C07D 311/58* (2006.01)
*C09B 61/00* (2006.01)
*A23L 2/04* (2006.01)
*A23L 2/58* (2006.01)
*B01D 15/36* (2006.01)

(52) U.S. Cl.
CPC .............. *C09B 61/00* (2013.01); *A23L 2/04* (2013.01); *A23L 2/58* (2013.01); *A23L 5/43* (2016.08); *B01D 15/362* (2013.01); *C07D 311/58* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 3,361,631 A | 1/1968 | Weinstein | |
| 3,456,050 A | 7/1969 | Rieckmann et al. | |
| 3,480,468 A | 11/1969 | Carletti et al. | |
| 4,172,902 A | 10/1979 | Asen et al. | |
| 4,640,218 A | 2/1987 | Motoyama et al. | |
| 4,681,766 A | 7/1987 | Huzinec et al. | |
| 4,878,921 A | 11/1989 | Koga et al. | |
| 6,541,048 B2 | 4/2003 | Zyck et al. | |
| 6,572,900 B1 | 6/2003 | Zyck et al. | |
| 6,572,906 B1 | 6/2003 | Higashimura et al. | |
| 6,881,430 B2 | 4/2005 | Kohler et al. | |
| 6,939,572 B2 | 9/2005 | Nguyen | |
| 6,994,889 B2 | 2/2006 | Satomi et al. | |
| 7,144,593 B2 | 12/2006 | Yukawa et al. | |
| 7,192,456 B2 | 3/2007 | Ichi et al. | |
| 7,229,490 B2 | 6/2007 | Isager et al. | |
| 7,261,769 B2 | 8/2007 | Bhaskaran et al. | |
| 7,279,189 B2 | 10/2007 | Lauro | |
| 7,338,791 B2 | 3/2008 | Koffas et al. | |
| 7,378,118 B2 | 5/2008 | Song et al. | |
| 8,053,634 B2 | 11/2011 | Tanaka et al. | |
| 8,361,167 B2 | 1/2013 | Blackburn et al. | |
| 8,425,960 B2 | 4/2013 | Inisan et al. | |
| 8,557,319 B2 | 10/2013 | Wu et al. | |
| 8,575,334 B2 | 11/2013 | Giusti et al. | |
| 8,642,340 B2 | 2/2014 | Mathews et al. | |
| 8,765,180 B2 | 7/2014 | Kochler et al. | |
| 8,962,327 B2 | 2/2015 | Yoon et al. | |
| 2004/0022904 A1* | 2/2004 | Nguyen | A23G 3/36 426/103 |
| 2004/0105919 A1 | 6/2004 | Chisholm | |
| 2005/0208189 A1 | 9/2005 | Kurschner et al. | |

(Continued)

FOREIGN PATENT DOCUMENTS

| | | |
|---|---|---|
| EP | 1279703 | 1/2003 |
| EP | 2545787 | 1/2013 |

(Continued)

OTHER PUBLICATIONS

McCallum, et al., "Improved High Performance Liquid Chromatographic Separation of Anthocyanin Compounds from Grapes using a Novel Mixed-Mode Ion-Exchange Reversed-Phase Column", J. Chromatography A., 2007, p. 38-45, vol. 1148.
Anonymous: "Blaukraut, Rotkraut und Rotkohl- 3 Namen für ein Gemüse," Farben und Leben Online, Mar. 10, 2010, Retrieved from the Internet: URL:http://web.archive.org/web/20100310100941/ http://www.farbenundleben.de/kultur/blaukraut.htm [retrieved on Sep. 5, 2016] p. 2. (with English translation retrieved on Oct. 19, 2016).
International Search Report and Written Opinion mailed Sep. 14, 2016 in International Application No. PCT/US2016/040563.
Sigurdson et al., "Evaluating the role of metal ions in the bathochromic and hyperchromic responses of cyanidin derivatives in acidic and alkaline pH," Food Chemistry 208:26-34 (Mar. 29, 2016).

*Primary Examiner* — Golam M M Shameem
*Assistant Examiner* — Laura Daniel
(74) *Attorney, Agent, or Firm* — Baker Botts L.L.P.

(57) ABSTRACT

The present invention is directed to a method of isolating fractions of anthocyanin molecules from anthocyanin-containing vegetable and fruit juices and extracts, or combinations thereof, at a select pH based on differences in polarity of the anthocyanin molecules in the anthocyanin-containing vegetable and fruit juices and extracts.

16 Claims, 10 Drawing Sheets

(56) References Cited

U.S. PATENT DOCUMENTS

| | | |
|---|---|---|
| 2008/0160084 A1 | 7/2008 | Huynh et al. |
| 2009/0298952 A1 | 12/2009 | Brimmer et al. |
| 2011/0129584 A1 | 6/2011 | Myers et al. |
| 2012/0034658 A1 | 2/2012 | Yoon et al. |
| 2013/0165531 A1 | 6/2013 | Shi et al. |
| 2013/0184359 A1 | 7/2013 | Nafisi-Movaghar |
| 2013/0202703 A1 | 8/2013 | Sadano |
| 2013/0216665 A1 | 8/2013 | Mason et al. |
| 2014/0161938 A1 | 6/2014 | Braga et al. |
| 2016/0015067 A1 | 1/2016 | Robbins et al. |

FOREIGN PATENT DOCUMENTS

| | | |
|---|---|---|
| JP | H07-188572 A | 7/1995 |
| JP | 2010-522794 A | 7/2010 |
| WO | 9507622 | 3/1995 |
| WO | WO 03/064538 A1 | 8/2003 |
| WO | 2005007088 | 1/2005 |
| WO | WO 2008/111589 A1 | 9/2008 |
| WO | 2009071148 | 6/2009 |
| WO | 2009100165 | 8/2009 |
| WO | 2010114568 | 10/2010 |
| WO | 2010131049 | 11/2010 |
| WO | WO 2012/043173 A1 | 4/2012 |
| WO | 2012172429 | 12/2012 |
| WO | 2013106179 | 7/2013 |
| WO | WO 2014/023712 A1 | 2/2014 |
| WO | 2014150230 | 9/2014 |
| WO | 2014152417 | 9/2014 |
| WO | 2014152478 | 9/2014 |

\* cited by examiner

METHOD OF ISOLATING BLUE ANTHOCYANIN FRACTIONS

This application is a 371 National Stage filing of International Application Serial No. PCT/US2014/027319 filed Mar. 14, 2014, which claims benefit of U.S. Provisional Patent Application Ser. No. 61/790,842 filed Mar. 15, 2013, all of which are hereby incorporated herein by reference in their entirety.

BACKGROUND OF THE INVENTION

Field of the Invention

The present invention relates to a method of obtaining natural blue anthocyanin-containing colorant compositions by selectively isolating fractions of anthocyanin molecules from anthocyanin-containing vegetable and fruit juices and extracts.

Description of the Related Art

There is increasing interest in the food industry to replace synthetic materials for coloring foods with natural colorants.

One challenge in replacing synthetic colorants with natural colorants has been identifying natural colorants that provide color characteristics similar to those provided by synthetic colorants.

Natural colorants that provide the same color characteristics as the synthetic blue colorant, FD&C Blue No. 1, have not been found, to this time. The lack of appropriate natural cyan blue hue colorants has also made it challenging to obtain desired natural green hue colorants from the blending of natural blue and yellow colorants. Spirulina Blue, a blue-green algae-derived material, is used as a natural blue colorant, but does not provide the same color characteristics as FD&C Blue No. 1.

Anthocyanins are water-soluble compounds found in the cell vacuoles of fruits, vegetables, and flower petals, and sometimes, roots, leaves, stems, and bracts of plants. At least in part due to their wide availability, anthocyanin-containing vegetable and fruit juices and extracts have been used as natural, edible colorants and to produce colorant compositions, in particular, natural red, purple, and blue hue colorant compositions.

An anthocyanin comprises an anthocyanidin (the aglycone) esterified to one or more sugar molecules (the glycone(s)) to form a glycoside. Sugar molecules may be attached at the C-3, C-5, C-7, C-3', C-4', and/or C-5' positions. Examples of sugar molecules found in anthocyanin structures are arabinose, galactose, glucose, rhamnose, rutinose, sambubiose, sophorose, and xylose.

Anthocyanins may also be acylated, i.e., they may have one or more molecules esterified to the sugar molecules, typically at the 6-position of a monosaccharide, but also potentially at the 2-, 3-, or 4-positions. The most common acyl units include those derived from coumaric, ferulic, caffeic, sinapic, gallic, malonic, acetic, malic, succinic, vanillic, and oxalic acids.

The structure of an anthocyanidin is shown below in the flavylium cation form, which is the primary form under acidic conditions. The anthocyanidin may be substituted with hydrogen, hydroxyl, and/or methoxyl groups at various positions:

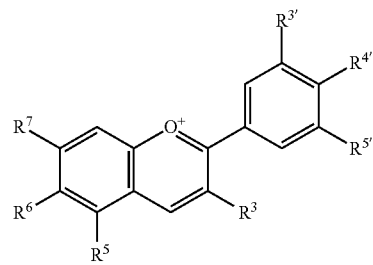

wherein $R^3$ is H or OH,
$R^5$ is H, OH, or $OCH_3$,
$R^6$ is H or OH,
$R^7$ is OH or $OCH_3$,
$R^{3'}$ is H, OH, or $OCH_3$,
$R^{4'}$ is OH or $OCH_3$, and
$R^{5'}$ is H, OH, or $OCH_3$.

The most common anthocyanidins in nature are shown by the following structures:

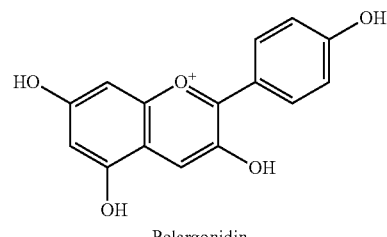
Pelargonidin

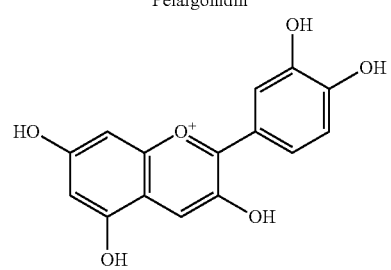
Cyanidin

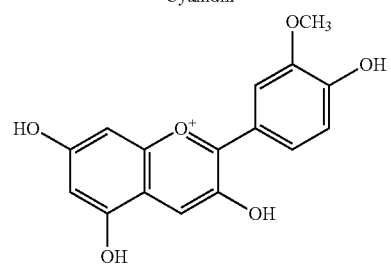
Peoridin

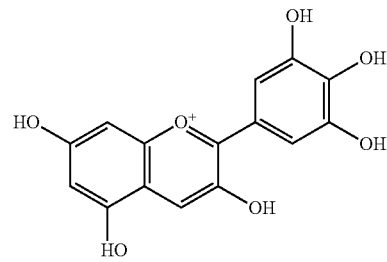
Delphinidin

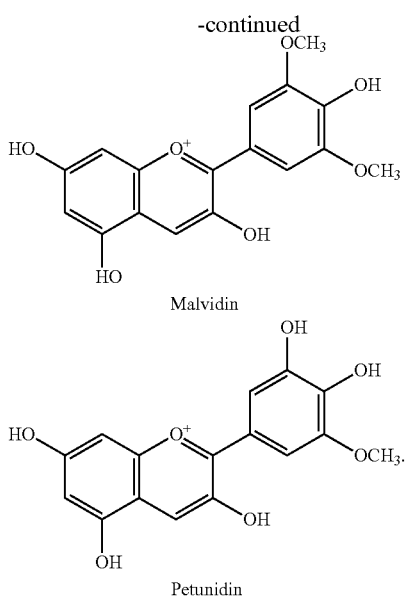

Malvidin

Petunidin

Therefore, the class of compounds known as anthocyanins encompasses an enormous number of structurally diverse compounds based on differences in primary structure, glycosylation and acylation patterns.

Known plant sources of anthocyanins include: (1) vegetables such as red cabbage, purple sweet potato, blue potato, red potato, red radish, black carrot, purple carrot, purple corn, red corn, red onion, purple broccoli, red broccoli, purple cauliflower, rhubarb, black bean, red leaf lettuce, black rice and eggplant; and (2) fruits such as strawberry, raspberry, cranberry, lingonberry, red grape, apple, black currant, red currant, cherry, blueberry, elderberry, bilberry, crowberry, blackberry, chokeberry, gooseberry, açaí, nectarine, peach, plum, blood orange and blue tomato. Each anthocyanin source contains different amounts of multiple, distinct anthocyanin species, with 15 to 30 structurally distinct anthocyanin molecules being common for a given plant source.

The color characteristics of anthocyanin-containing vegetable and fruit juices and extracts change as a result of changing pH. Anthocyanin-containing juices and extracts generally exhibit red hues at low pH, and the hue shifts to purple as the pH is increased. Only a few juices and extracts exhibit a blue hue as pH is increased further.

The change in color of anthocyanin-containing juices and extracts resulting from changes in pH is related to the numerous secondary structures of anthocyanins that may exist in equilibrium with the primary flavylium cation structure in aqueous solution. When pH is changed, the relative quantities of the different equilibrium structures will change. At a given pH, one or more structural forms may predominate, while others are present in low quantities or not present. For example, at very low pH, the flavylium cation form predominates. As pH is increased, molecules in the flavylium cation form may be deprotonated and converted to the carbinol pseudobase form, which may be further converted through loss of a water molecule and a proton to the neutral and ionized quinonoidal base forms, respectively, and further, to the chalcone form. These transformations reduce the quantity of molecules in the flavylium cation form and increase the quantities in the other equilibrium forms to different extents. Therefore, the different equilibrium structures exist in different relative quantities at higher pH compared to low pH. Each structural form of anthocyanin may absorb light differently, resulting in a different perceived color, including no color. Therefore, as the pH of the solution is changed, changes in the relative quantities of the different structural forms may result in changes in the color of the solution.

Each distinct anthocyanin molecule is characterized by its own set of equilibrium molecular structures and equilibrium constants for the reactions that transform one structure into another. For example, the reaction transforming one anthocyanin equilibrium structure into another may have a particular acid dissociation constant, $K_a$, associated with it. The reaction may also be discussed in terms of the logarithmic constant, $pK_a$, which is defined as—$\log_{10} K_a$.

The flavylium cation and quinonoidal base structures have conjugated bonds connecting all three rings of the anthocyanin molecules. The extensive delocalized pi bonds allow the flavylium cation and quinonoidal base to absorb visible light, resulting in the perceived red hue of the flavylium cation at low pH and the purple or blue hue of the ionized quinonoidal base at a higher pH. In contrast, the carbinol pseudobase and chalcone structures do not have delocalized pi bonds connecting all three rings and are colorless or slightly yellow.

The substitution pattern of anthocyanins also affects color. For example, it is generally observed that the hue shifts from pink to purple when hydrogen atoms are replaced with hydroxyl groups. Similarly, the number of glycosyl (sugar) units and the number and type of acyl units are observed to affect color. However, these phenomena are not well understood or predictable.

Additionally, intermolecular and intramolecular interactions also affect anthocyanin color. The same anthocyanin may produce different hues depending on the other molecules present. For example, it is believed that acyl groups on the anthocyanin sugars can fold in and protect the flavylium cation C-2 position from nucleophilic attack. Therefore, this intramolecular interaction prevents formation of the colorless carbinol pseudobase structure. Similarly, it is believed that anthocyanin molecules self-associate, which is evidenced by the fact that a two-fold increase in anthocyanin concentration can cause a 300-fold increase in chroma, and can change the hue and value as well. It is hypothesized that this self-association is similar to intramolecular stacking, and prevents nucleophilic attack and formation of the carbinol pseudobase structure.

Although it is known that factors such as pH, anthocyanin chemical structure, substituent patterns, inter- and intramolecular interactions all impact the color observed in anthocyanin-containing vegetable and fruit juices and extracts, it is not well understood how these factors interact to alter color; i.e., the specific cause and effect are not predictable.

For example, individual anthocyanin molecules have been separated by HPLC, but the separation has always occurred at low pH, and the color characteristics of individual anthocyanins were analyzed at low pH. Similarly, the effect of pH on the color characteristics of anthocyanin-containing vegetable and fruit juices and extracts has been studied, but these studies have analyzed the complex mixtures of anthocyanins naturally occurring in the juices and extracts. How changing pH affects the color characteristics of individual anthocyanin molecules or fractions of anthocyanins separated from natural sources, however, is not well understood or predictable. The prior art discloses that the number and types of substituents, e.g., the sugar and acyl groups, impact color; however, it does not disclose and it is not known how these substituents affect color as pH changes. Finally, although the prior art hypothesizes that various inter- and intra-molecular interactions affect color, it does not disclose how changing pH affects these inter- and intra-molecular interactions and, ultimately, the observed color of the anthocyanins.

WO 2009/100165 A2 discloses a method of separating anthocyanins from other phenolic molecules in the juice of anthocyanin-containing fruits and vegetables. WO 2009/100165 A2 does not disclose selectively separating fractions of anthocyanin molecules based on differences in charge and polarity of the molecules to produce fractions with a desired color that is different than the anthocyanin-containing juice.

The separation of individual anthocyanins at analytical scale is described in J. Chromatography A., 1148 (2007), 38-45. The separation is conducted at low pH, i.e., pH of less than 2, using HPLC in order to assist in identifying individual anthocyanins. This method separates anthocyanin molecules for detection rather than producing fractions with mixtures of anthocyanins.

WO 2004/012526 discloses a blue colorant solution of red cabbage anthocyanins at a pH of 7.9 that is used in a sugar-syrup for coating confectionery cores. The red cabbage anthocyanins were not separated into fractions.

There is no example in the prior art of isolating fractions of anthocyanin molecules from anthocyanin-containing vegetable and fruit juices and extracts at a select pH based on differences in charge and polarity of the anthocyanin molecules. In addition, methods for obtaining anthocyanin fractions that provide different color characteristics than those provided by the source juices and extracts have not been disclosed. In particular, the prior art has not described a method for obtaining a natural blue anthocyanin-containing colorant composition providing color characteristics similar to those provided by the synthetic blue colorant, FD&C Blue No. 1.

It is desirable to have a broad palette of natural colorants available for coloring foods. There is a long-felt need for natural blue colorants that provide color characteristics similar to those provided by synthetic FD&C Blue No. 1. Therefore, a method of obtaining such natural blue colorants from anthocyanin-containing vegetable and fruit juices and extracts is desired.

SUMMARY OF THE INVENTION

The present invention is directed to a method of obtaining natural blue anthocyanin-containing colorant compositions providing color characteristics similar to those provided by the synthetic blue colorant, FD&C Blue No. 1. The natural blue anthocyanin-containing colorant is obtained from anthocyanin-containing vegetable and fruit juices and extracts by isolating fractions containing a mixture of anthocyanin molecules at a select pH based on differences in charge and polarity of the anthocyanin molecules.

In an embodiment, the invention is directed to a method of isolating a fraction of anthocyanins from an anthocyanin-containing vegetable or fruit juice or extract, or a combination thereof comprising: a) loading an anthocyanin-containing vegetable or fruit juice or extract, or a combination thereof, on an ion exchange column; b) selectively separating anthocyanins on the ion exchange column based on differences in charge and polarity of the anthocyanin molecules using a solvent of select pH, wherein the pH value is at least about 2; and c) selecting one fraction or a combination of fractions containing separated anthocyanins, such that the separated anthocyanins in the one fraction or the combination of fractions, when in an aqueous solution at pH 8.0 has a maximum absorbance of 615 nm to 635 nm. The selected anthocyanin-containing fraction or combination of fractions contain separated anthocyanins that provide color characteristics closer to those provided by FD&C Blue No. 1, but are different, i.e., a fractionated subset, from that of the anthocyanin-containing vegetable or fruit juice or extract, or the combination thereof.

BRIEF DESCRIPTION OF THE DRAWINGS

FIG. 9 also allows for a visual comparison of the colors provided by the 520-nm and 530-nm Fractions with the color of a confectionery product panned with a sugar-syrup colored with FD&C Blue No. 1.

FIG. 10 shows that the 520-nm and 530-nm Fractions each contain three distinct anthocyanin compounds and identifies the functional groups and sugars on the anthocyanin compounds.

DETAILED DESCRIPTION OF THE INVENTION

Figure 1:
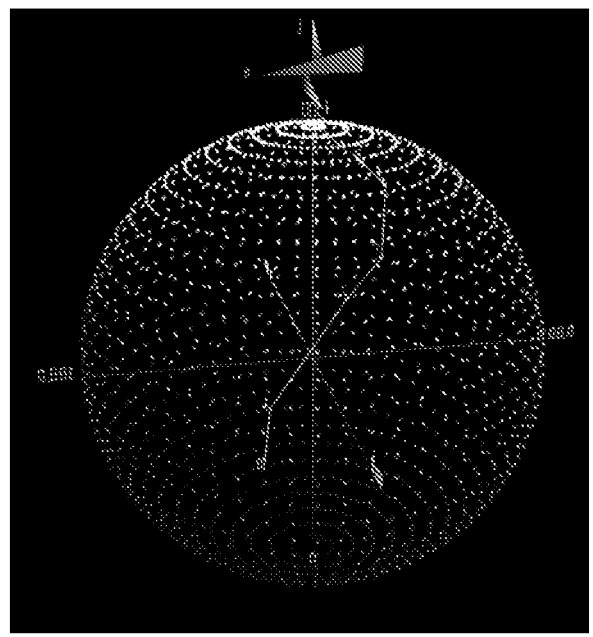
FIG. 1 shows two perspectives of a three dimensional representation of the color characteristics provided by FD&C Blue No. 1 in CIE 1976 CIELAB L*a*b* color space as a function of concentration in aqueous solution.
Figure 1:
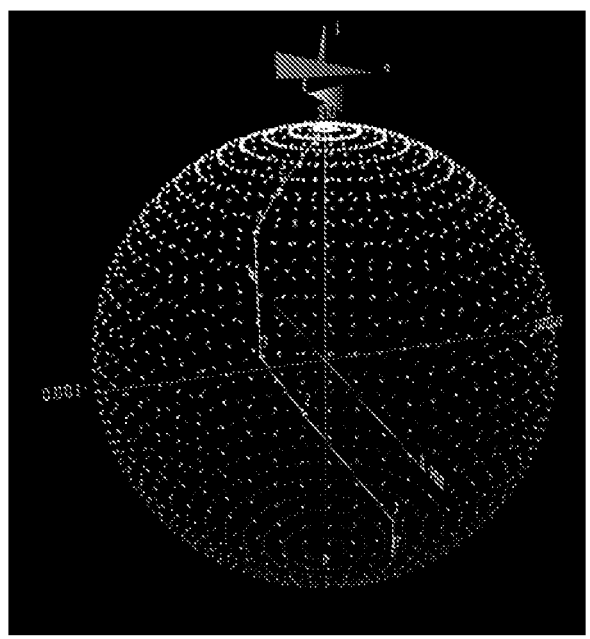

Anthocyanin-containing vegetable and fruit juices and extracts are presently used as natural, edible colorants and to produce colorant compositions, in particular, natural red, purple, and blue hue colorant compositions. The juices and extracts contain a mixture of all the anthocyanin molecules naturally present in the vegetable and fruit sources, along with numerous other classes of compounds. Therefore, the presently available anthocyanin colorants are limited to those colors associated with the mixtures of anthocyanins that naturally exist in the vegetable and fruit sources. The invention involves methods of isolating mixtures of anthocyanin molecules different from the complex mixture of anthocyanins naturally present in vegetable and fruit juices and extracts. The method involves isolating fractions of anthocyanin molecules from the complex mixture in the vegetable and fruit juices and extracts at a select pH based on differences in the charge and polarity of the anthocyanin molecules.

One aspect of the invention involves isolating fractions of anthocyanin molecules from anthocyanin-containing vegetable and fruit juices and extracts to obtain colorant compositions providing specific, targeted color characteristics similar to those provided by the synthetic blue colorant, FD&C Blue No. 1. As used herein, providing color characteristics "similar" to FD&C Blue No. 1 means the color is closer in color characteristics than any other natural colorant, such as for example, Spirulina Blue.

The applicants discovered that separating anthocyanins using a solvent at a select pH and differences in polarity of the anthocyanin molecules would yield fractions containing mixtures of anthocyanins providing color characteristics similar to those provided by the synthetic blue colorant, FD&C Blue No. 1. Each anthocyanin source contains different amounts of multiple, distinct anthocyanin molecules, and each molecule may exist in equilibrium with one or more secondary structures. There may be differences in charge and/or polarity among the different anthocyanin molecules and their equilibrium molecular structures. Through separation based on differences in charge and polarity of the anthocyanin molecules at a select pH, the applicants were able to isolate fractions of anthocyanins with distinct spectral characteristics from a complex mixture of anthocyanins. The spectral characteristics of the fractions were different and not evident from the spectral characteristics of the complex mixture of anthocyanins found in the juice or extract. The applicants have identified anthocyanin fractions that provide color characteristics closer to those provided by synthetic FD&C Blue No. 1 than any known natural blue colorant can provide, including Spirulina Blue.

An "anthocyanin-containing vegetable or fruit juice" may be obtained by pressing liquid out of the fruit or vegetable. An "anthocyanin-containing vegetable or fruit extract" may be obtained by washing a macerated fruit or vegetable with a solvent (e.g., water, alcohol). Juices and extracts contain anthocyanins as well as many other naturally occurring compounds, including, for example, carbohydrates, acids, flavonoids, metal ions, phenolic acids, phenolic acid esters, and vitamins. The term, "vegetable or fruit juice or extract," is equivalent to the list of terms, "vegetable juice, fruit juice, vegetable extract, or fruit extract," and includes processed juices and extracts, including, for example, reconstituted juices and extracts, deodorized juices and extracts, and juices and extracts subjected to other processes for removing specific or broad classes of compounds.

"Fractionation" is the process of selecting and separating a portion of anthocyanins from the complex mixture of anthocyanins in an anthocyanin-containing vegetable or fruit juice or extract. The source of anthocyanins used in the method of the invention is an anthocyanin-containing vegetable or fruit juice or extract that provides blue hues at high pH values. In some embodiments, the source of anthocyanins used in the method of the invention is red cabbage, purple sweet potato, blue potato, purple carrot or black carrot, or a combination thereof.

A "fraction" is the product of fractionation. An "anthocyanin fraction" contains a mixture of anthocyanins that is different from the mixture of anthocyanins in the anthocyanin-containing juice or extract from which the fraction was separated. Anthocyanin fractions are separated from the juice or extract at a select pH based on differences in charge and polarity of the different anthocyanin molecules present.

A "select pH" is a pH of 2 or higher, e.g. a pH in a range of about 2 to about 9, both in the context of separating and performing color characterization of anthocyanins. In other embodiments the pH may be at a pH of 3 or higher, 4 or higher, 5 or higher, 6 or higher, or 7 or higher, e.g., a pH in one of the following respective ranges, i.e., about 3 to about 9, about 4 to about 9, about 5 to about 9, about 6 to about 9 or about 7 to about 9.

"Maximum absorbance," "lambda max," or "$\lambda_{max}$," is the wavelength in nanometers at which the maximum fraction of light is absorbed by a substance. In general, the maximum absorbance can be used as a characteristic value to compare substances when measured with a UV/Visible spectrophotometer or colorimeter.

References to "FD&C Blue No. 1" include the different names given to the identical synthetic blue colorant, Brilliant Blue FCF and European Commission E133. The lambda max of FD&C Blue No. 1 is 630 nm.

A "colorant" is any substance that imparts color by absorbing or scattering light at different wavelengths. A "natural colorant" is a colorant that exists in or is produced by nature or is sourced therefrom. A "blue colorant" is a colorant that reflects light at wavelengths in the region of 450-495 nanometers and has a maximum UV/VIS wavelength absorbance ranging from 615 to 635 nanometers. A "natural anthocyanin-containing colorant" is a natural colorant comprising anthocyanins sourced from plants.

The natural anthocyanin-containing colorant is a composition that may comprise only anthocyanins or may also include other plant components. The composition may take the form of a solid, e.g., a powder, or a liquid solution, e.g., an aqueous liquid.

In an embodiment, the invention is directed to a method of isolating a fraction of anthocyanins from an anthocyanin-containing vegetable or fruit juice or extract, or a combination thereof, comprising: a) loading an anthocyanin-containing vegetable or fruit juice or extract, or a combination thereof, on an ion exchange column; b) selectively separating anthocyanins on the ion exchange column based on differences in charge and polarity of the anthocyanin molecules using a solvent of a select pH; and c) selecting one fraction or a combination of fractions containing separated anthocyanins, such that the separated anthocyanins in the one fraction or the combination of fractions, when in an aqueous solution at pH 8.0 has a maximum absorbance of 615 nm to 635 nm. In an embodiment, the anthocyanin-containing fraction is separated from the anthocyanin-containing vegetable or fruit juice or extract with a solvent at a pH from a range of about 2 to about 9, or in one of the following ranges, i.e., about 3 to about 9, about 4 to about 9, about 5 to about 9, about 6 to about 9 or about 7 to about 9.

"Hue" refers to the color property that gives a color its name, for example red, orange-red, blue, violet, etc.

"Chroma" is a color property indicating the purity of a color, where higher chroma is associated with greater purity of hue and less dilution by white, gray, or black.

"Value" is a color property indicating the lightness or darkness of a color, where higher value is associated with greater lightness.

The terms "color" and "color characteristics" are used interchangeably, and encompass color properties such as hue, chroma, and value and color model system parameters used to describe these properties, such as Commission Internationale de l'Eclairage CIE 1976 CIELAB color space L*a*b* values and CIELCH color space L*C*h° values. The CIELAB and CIELCH color models provide more perceptually uniform color spaces than earlier color models. Colorants are analyzed with a spectrophotometer, and CIELAB L*a*b* and CIELCH L*C*h° values are calculated from the spectral data. The L*a*b* and L*C*h° values provide a means of representing color characteristics and assessing the magnitude of difference between two colors. The CIELAB L*a*b* and CIELCH L*C*h° values presented herein, in all instances unless stated otherwise, were calculated from spectral data obtained from a Konica Minolta Spectrophotometer CM-3500d operated in transmittance mode, with CIE Standard Illuminant D65 and 10 degree observer angle.

L*a*b* values consist of a set of coordinate values defined in a three-dimensional Cartesian coordinate system. L* is the value, or lightness, coordinate. L* provides a scale of lightness from black (0 L* units) to white (100 L* units) on a vertical axis. a* and b* are coordinates related to both hue and chroma. a* provides a scale for greenness (−a* units) to redness (+a* units), with neutral at the center point (0 a* units), on a horizontal axis. b* provides a scale for blueness (−b* units) to yellowness (+b* units), with neutral at the center point (0 b* units), on a second horizontal axis perpendicular to the first horizontal axis. The three axes cross where L* has a value of 50 and a* and b* are both zero.

L*C*h° values consist of a set of coordinate values defined in a three-dimensional cylindrical coordinate system. L* is the value, or lightness, coordinate. L* provides a scale of lightness from black (0 L* units) to white (100 L* units) on a longitudinal axis. h° is the hue coordinate. h° is specified as an angle from 0° to 360° moving counterclockwise around the L* axis. Pure red has a hue angle of 0°, pure yellow has a hue angle of 90°, pure green has a hue angle of 180°, and pure blue has a hue angle of 270°. The C* coordinate represents chroma and is specified as a radial distance from the L* axis. C* provides a scale from achromatic, i.e., neutral white, gray, or black, at the L* axis (0 C* units) to greater purity of hue as the coordinate moves away from the L* axis (up to 100 or more C* units). C* and h° can be calculated from a* and b* using Equations 1 and 2:

$$C^* = (a^{*2} + b^{*2})^{0.5} \quad (1)$$

$$h° = \arctan\left(\frac{b^*}{a^*}\right) \quad (2)$$

"Delta E," "$\Delta E_{ab}^*$," or "$\Delta E$" is a measure of the magnitude of total color difference between two colors represented in CIELAB L*a*b* color space. It has been reported that an experienced color observer cannot distinguish any difference between two colors when the $\Delta E$ is about 2.3 or less. The $\Delta E$ of two different colors with L*a*b* values, $L^*_1 a^*_1 b^*_1$ and $L^*_2 a^*_2 b^*_2$, is calculated using Equation 3:

$$\Delta E_{ab}^* = \sqrt{(L^*_1 - L^*_2)^2 + (a^*_1 - a^*_2)^2 + (b^*_1 - b^*_2)^2} \quad (3)$$

The CIELAB L*a*b* and CIELCH L*C*h° values of FD&C Blue No. 1 at seven different concentrations in aqueous solution are presented in Table 1. These values were calculated from spectral data obtained with a Konica Minolta Spectrophotometer CM-3500d using the transmittance setting.

TABLE 1

| Concentration | L* | a* | b* | C* | h° |
|---|---|---|---|---|---|
| 1000 ppm | 10.49 | 15.82 | −44.99 | 47.69 | 289.37 |
| 500 ppm | 24.07 | 9.80 | −58.18 | 59.00 | 279.56 |
| 100 ppm | 52.43 | −29.57 | −57.38 | 64.55 | 242.74 |
| 50 ppm | 63.64 | −43.71 | −48.31 | 65.14 | 227.86 |
| 10 ppm | 84.25 | −37.23 | −23.42 | 43.99 | 212.17 |
| 5 ppm | 90.65 | −24.40 | −14.28 | 28.27 | 210.33 |
| 1 ppm | 97.69 | −6.43 | −3.57 | 7.36 | 209.02 |

These L*a*b* and L*C*h° values for FD&C Blue No. 1 represent the ideal target values for a natural blue colorant alternative to FD&C Blue No. 1. Natural blue colorants having L*a*b* values that fall within a $\Delta E$ of 2.3 or less from these target values would be expected to provide color characteristics sufficiently similar to those provided by FD&C Blue No. 1 that a human eye could not distinguish the difference in color provided by the natural colorant versus the synthetic. Clearly, the closer the L*a*b* values for a natural blue colorant come to the synthetic target values (i.e., yielding smaller values of $\Delta E$), the better replacement the natural blue colorant will be for FD&C Blue No. 1 in an edible application.

Figure 2:
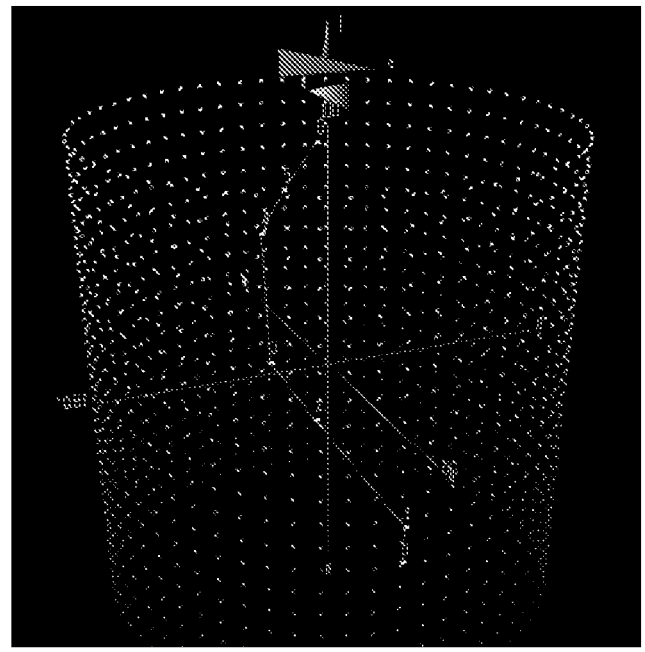
FIG. 2 shows two perspectives of a three dimensional representation of the color characteristics provided by FD&C Blue No. 1 in CIE 1976 CIELCH L*C*h° color space as a function of concentration in aqueous solution.
Figure 2:
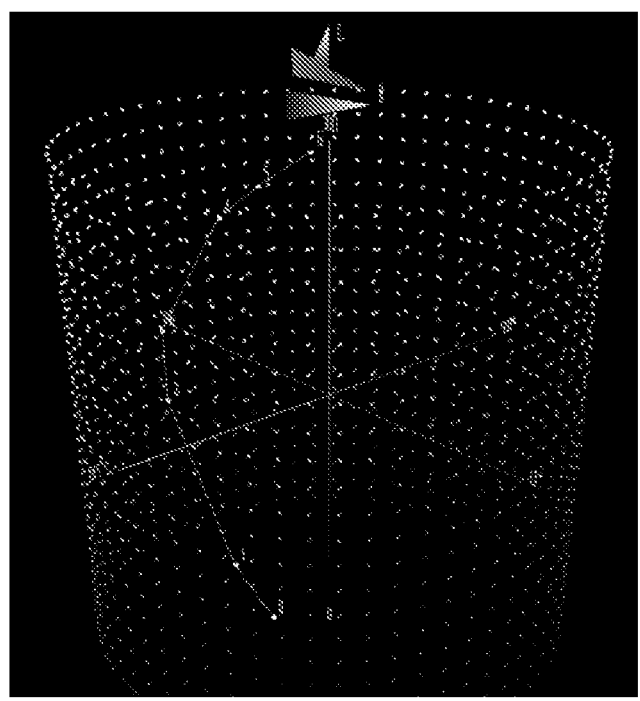

FIG. 1 shows two perspectives of a three dimensional representation of the L*a*b* values for aqueous solutions of FD&C Blue No. 1 at the seven concentrations reported in Table 1, connected by line segments. FIG. 2 shows two perspectives of a three dimensional representation of the L*C*h° values for aqueous solutions of FD&C Blue No. 1 at the seven concentrations reported in Table 1, connected by line segments.

Mathematical models can be generated to represent the color characteristics provided by FD&C Blue No. 1 at any concentration in the L*a*b* and L*C*h* color spaces. For example, the color characteristics may be represented by a segmented line model connecting the L*a*b* or L*C*h° data points of Table 1. A line (L) connecting two points ($P^1$ and $P^2$) representing two different concentrations of FD&C Blue No. 1 in L*a*b* space can be calculated with the following Equation 4:

$$L = \{P_1 + t^*(P_2 - P_1)\} \quad (4)$$

wherein $P_1$ is ($L^*_1$, $a^*_1$, $b^*_1$); $P_2$ is ($L^*_2$, $a^*_2$, $b^*_2$); and t is any real number.

Consequently, a segmented line model for FD&C Blue No. 1 in L*a*b* color space can be interpolated based on the L*a*b* values for the seven different concentration points using Equation 4 as follows:

For concentrations between 500 and 1000 ppm, 0<t<1:
L*=10.49+13.58*t
a*=15.82+−6.02*t
b*=−44.99+−13.19*t For concentrations between 100 and 500 ppm, 0<t<1:
L*=24.07+28.36*t
a*=9.80+−39.37*t
b*=−58.18+0.80*t For concentrations between 50 and 100 ppm, 0<t<1:
L*=52.43+11.21*t
a*=−29.57+−14.14*t
b*=−57.38+9.07*t For concentrations between 10 and 50 ppm, 0<t<1:
  $L^* = 63.64 + 20.61 \cdot t$
  $a^* = -43.71 + 6.48 \cdot t$
  $b^* = -48.31 + 24.89 \cdot t$
For concentrations between 5 and 10 ppm, 0<t<1:
  $L^* = 84.25 + 6.40 \cdot t$
  $a^* = -37.23 + 12.83 \cdot t$
  $b^* = -23.42 + 9.14 \cdot t$
For concentrations between 1 and 5 ppm, 0<t<1:
  $L^* = 90.65 + 7.04 \cdot t$
  $a^* = -24.40 + 17.97 \cdot t$
  $b^* = -14.28 + 10.71 \cdot t$ The segmented line model for FD&C Blue No. 1 in L*a*b* space is drawn in FIG. 1.

Figure 3:
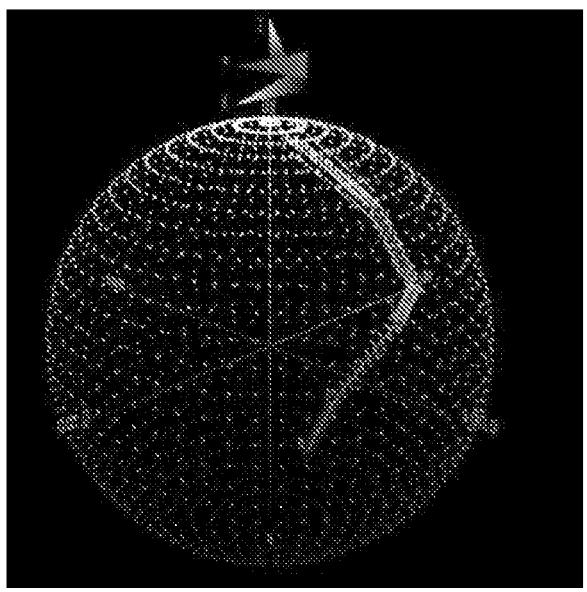
FIG. 3 represents two perspectives of the area in CIE 1976 CIELAB L*a*b* color space of colors that differ from the colors provided by FD&C Blue No. 1 by a ΔE of 3 or less and an illustration of a segmented tube defined by the color space data.
Figure 3:
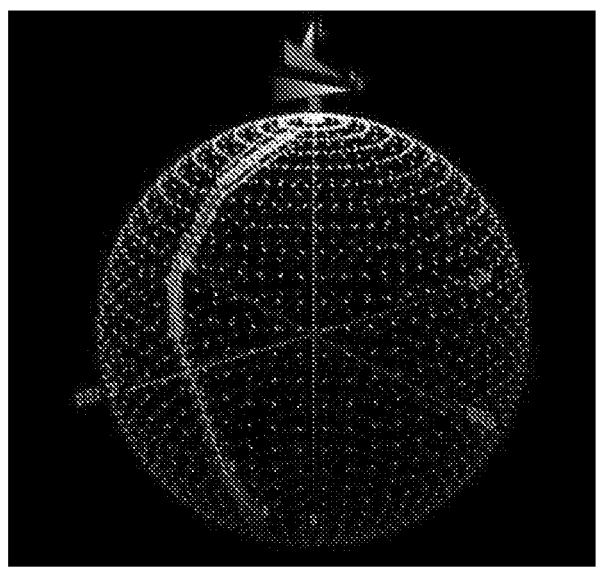
Figure 3:
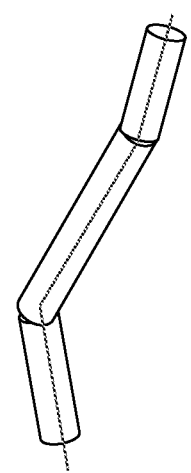

In addition, colors having L*a*b* values falling within a specific ΔE range of the FD&C Blue No. 1 model can be mathematically modeled in L*a*b* color space. Selecting a specific ΔE value, e.g., 3, with respect to FD&C Blue No. 1 and plotting that ΔE in L*a*b* color space results in a tube-like structure around the FD&C Blue No. 1 model, as shown in FIG. 3. It is noted that any color with a ΔE value of about 2.3 or less from any point on the model will not be distinguishable from the color provided by FD&C Blue No. 1.

To determine whether a point ($X_0$) in L*a*b* color space falls within a specific ΔE value from the FD&C Blue No. 1 model, the minimum distance, $d_{min}$, between the point and the model (represented by line segment $X_1$ to $X_2$) must be calculated.

Equation 5 can be used to calculate $d_{min}$:

$$d_{min} = \frac{|(x_0 - x_1) \times (x_0 - x_2)|}{|x_2 - x_1|} \quad (5)$$

wherein x denotes the cross product of two vectors and vertical bars denote the magnitude of a vector expression.

If the value of $d_{min}$ is less than or equal to the chosen ΔE value, then the point in L*a*b* color space falls within that specific ΔE value from the FD&C Blue No. 1 model.

For example, it may be determined whether Spirulina Blue provides a color having a ΔE of 12 or less compared to the color provided by FD&C Blue No. 1. Table 2 shows the color characteristics provided by Spirulina Blue, a known natural blue colorant, at two different concentrations in aqueous solution:

TABLE 2

| Concentration | L* | a* | b* | C* | h° |
|---|---|---|---|---|---|
| (404.8 mg/L) | 69.97 | −29.69 | −43.56 | 52.72 | 253.72 |
| (206 mg/L) | 80.3 | −23.97 | −29.39 | 37.92 | 230.8 |

The $X_0$ for the 404.8 mg/L Spirulina Blue solution in L*a*b* color space is:
  $X_0 = (69.97, -29.69, -43.56)$
The $X_0$ for the 206 mg/L Spirulina Blue solution in L*a*b* color space is:
  $X_0 = (80.3, -23.97, -29.39)$
$X_1$ and $X_2$ are two points from the FD&C Blue No. 1 model at 10 ppm and 50 ppm concentration in an aqueous solution, respectively:
  $X_1 = (63.64, -43.71, -48.31)$
  $X_2 = (84.25, -37.23, -23.24)$ The $d_{min}$, calculated using Equation 5, is 12.4 for the 404.8 mg/L Spirulina Blue solution and 14.4 for the 206 mg/L Spirulina Blue solution. Therefore, the Spirulina Blue solutions do not provide a color having a ΔE of 12 or less compared to the color provided by FD&C Blue No. 1 in aqueous solution when measured against the segmented line defined by the L*a*b* values for 10 ppm and 50 ppm FD&C Blue No. 1 in aqueous solution.

Spectral characteristics of a number of different solutions of Spirulina Blue were determined as shown in Table 3.

TABLE 3

Spirulina Solutions Data

| Data Name | ppm | L* (D65) | a* (D65) | b* (D65) | C* (D65) | h° (D65) |
|---|---|---|---|---|---|---|
| 0.04% Spirulina | 400 | 67.69 | −30.25 | −45.87 | 54.94 | 236.6 |
| 0.03% Spirulina | 300 | 72.77 | −29.43 | −39.52 | 49.27 | 233.32 |
| 0.02% Spirulina | 200 | 78.87 | −25.56 | −30.99 | 40.17 | 230.49 |
| 0.015% Spirulina | 150 | 82.98 | −21.82 | −25.29 | 33.4 | 229.22 |
| 0.01% Spirulina | 100 | 87.77 | −16.29 | −18.32 | 24.52 | 228.35 |
| 0.0075% Spirulina | 75 | 90.46 | −12.94 | −14.27 | 19.27 | 227.79 |
| 0.005% Spirulina | 50 | 93.23 | −9.26 | −10.13 | 13.72 | 227.59 |

Figure 5:
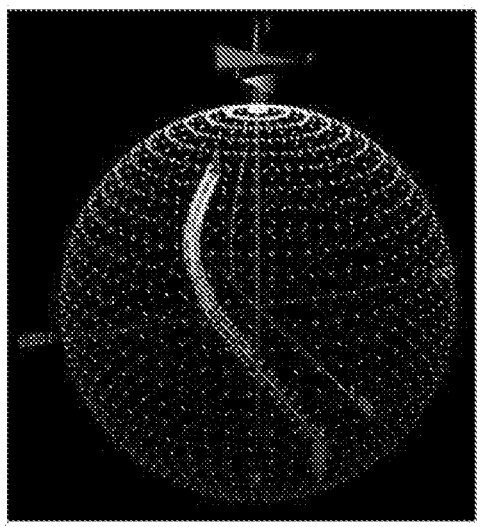
FIG. 5 shows two perspectives of a three dimensional representation of the color characteristics provided by FD&C Blue No. 1 in CIE 1976 CIELAB L*a*b* color space as a function of concentration in aqueous solution as well as the area of colors that differ from the colors provided by Blue No. 1 by a ΔE of 3 or less and also shows two perspectives of a three dimensional representation of the color characteristics provided by Spirulina Blue as a function of concentration in aqueous solution (white line closer to the x-axis).
Figure 5:
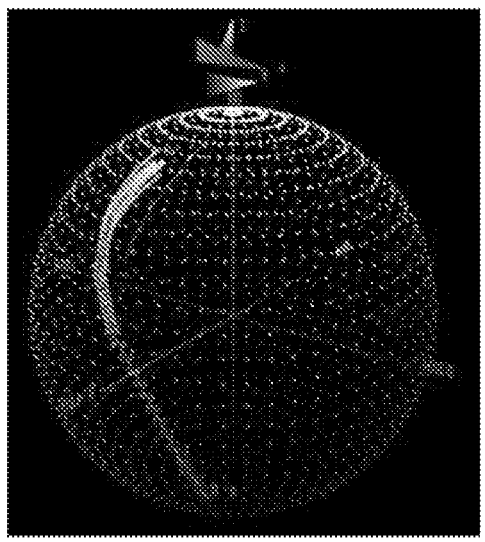

The data for Blue Spirulina has been plotted in the color graphs shown in FIG. 5 versus the FD&C Blue No. 1 data.

Differences between the color characteristics provided by Spirulina Blue and FD&C Blue No. 1 are represented in FIG. 5. FIG. 5 shows the segmented line model of the color characteristics provided by FD&C Blue No. 1 in L*a*b* color space at concentrations from 1 ppm to 1000 ppm in aqueous solution, with the model surrounded by a tube representing the area of colors that differ from the colors provided by Blue No. 1 by a ΔE of 3 or less. For comparison, FIG. 5 also shows a segmented line model of the color characteristics provided by Spirulina Blue in L*a*b* color space at concentrations from 50 ppm to 400 ppm in aqueous solution. The Spirulina Blue model does not intersect the Blue No. 1 model or associated tube at any point in L*a*b* color space.

The invention includes selecting a fraction or combination of fractions having natural blue anthocyanin-containing colorants sourced from vegetable, fruit or combinations thereof. The fraction or combination of fractions comprise a selectively separated mixture of anthocyanins, wherein at least one concentration of the colorant when in an aqueous solution at pH 8.0 provides color characteristics having a ΔE value of 12 or less compared to the color characteristics defined by the segmented line defined by the L*a*b* values of 5 ppm and 10 ppm FD&C Blue No. 1 in aqueous solution. In other embodiments the ΔE value may be less than 11, 10, 9, 8, 7, 6, 5, 4 or 3. The at least one concentration of colorant may also if desired be measured against a plurality of segmented lines defined by different concentrations of FD&C Blue No. 1 in aqueous solution, e.g., 1 and 5 ppm, 10 ppm and 50 ppm, 50 ppm and 100 ppm, 100 ppm and 500 ppm, 500 ppm and 1000 ppm, or any combination selected therefrom. For example, while not required, the at least one concentration of a colorant may be defined as having a ΔE value of 12 or less for a first segmented line at 5 ppm to 10 ppm, a ΔE value of 8 or less for a segmented line at 1 to 5 ppm and ΔE value of 12 or less for a segmented line at 10 ppm to 50 ppm. However, if ΔE value is used to describe the colorant of the invention, only one segmented line is required to define the colorant.

While Spirulina Blue is the natural colorant considered to provide the closest color match to FD&C Blue No. 1, the natural blue anthocyanin-containing colorant sourced from vegetable, fruit or combinations thereof that is a selectively separated mixture of anthocyanins in a fraction or combination of fractions obtained in accordance with the method of this invention is a better color match. In particular, when at least one concentration of the colorant in the selected fraction or combination of fractions is in an aqueous solution at pH 8.0, that colorant aqueous solution provides color characteristics matching a FD&C Blue No. 1 segmented line based on a series of aqueous solutions having differing concentrations of FD&C Blue No. 1 defined in an L*a*b* color space, wherein matching means the at least one concentration of the colorant in an aqueous solution at pH of 8.0 has a ΔE value measured against the FD&C Blue No. 1 segmented line that is at least one unit less than a ΔE value for a Spirulina Blue segmented line defined in the same L*a*b* color space based on a series of aqueous solutions having differing concentrations of Spirulina Blue measured against FD&C Blue No. 1 segmented line. In other embodiments the ΔE value of the at least one concentration of the colorant in an aqueous solution at pH of 8.0 measured against the FD&C Blue No. 1 segmented line is at least 2, 3, 4, 5 or 6 units less than a ΔE value for a Spirulina Blue segmented line measured against FD&C Blue No. 1 segmented line. In still other embodiments the ΔE value of the at least one concentration of the colorant in an aqueous solution at pH of 8.0 measured against the FD&C Blue No. 1 segmented line is at least 7, 8, 9, 10 or 11 units less than a ΔE value for a Spirulina Blue segmented line measured against FD&C Blue No. 1 segmented line.

Figure 4:
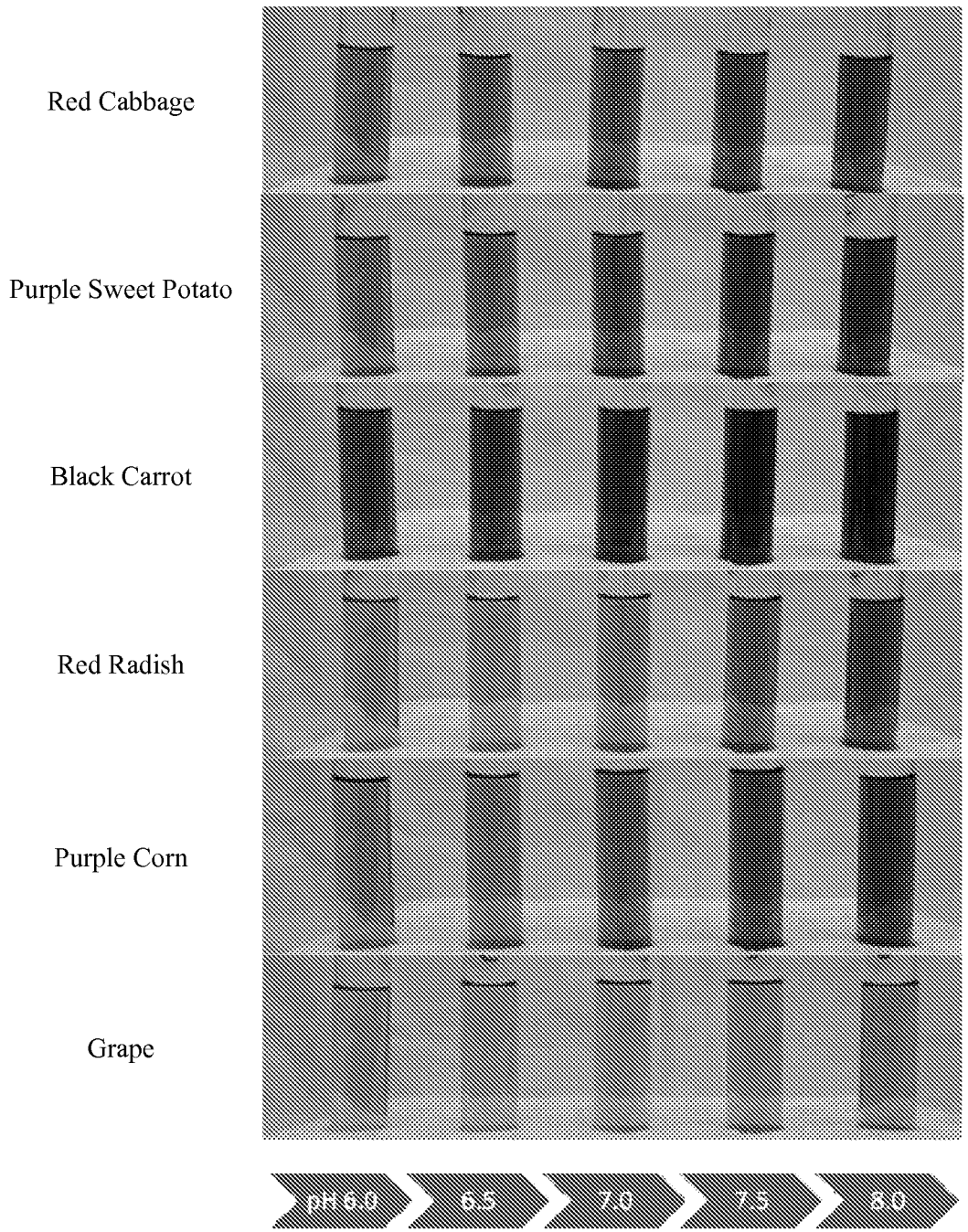
FIG. 4 shows a comparison of the colors provided by different fruit and vegetable extracts in aqueous solution at different pH values.

Various fruit and vegetable extracts containing anthocyanins were analyzed to identify a source of anthocyanins that would provide color characteristics closest to those provided by the synthetic blue colorant, FD&C Blue No. 1. FIG. 4 shows a comparison of six different commercially available extracts of red cabbage, purple sweet potato, black carrot, red radish, purple corn, and grape in aqueous solution at five different pH values. Visually, it can be seen that anthocyanins from red radish, purple corn, and grape did not provide blue hues in aqueous solution at any pH in the range from pH 6 to pH 8. Anthocyanins from red cabbage, purple sweet potato, and black carrot provided blue hues in aqueous solution at the higher end of the pH range.

Any anthocyanin-containing fruit or vegetable juice or extract that provides blue hues at high pH values may be used as a source of anthocyanins to produce anthocyanin fraction(s) of the invention. In some embodiments, the anthocyanin fraction is isolated from an extract of red cabbage, purple sweet potato, blue potato, purple carrot or black carrot, or a combination thereof.

In an embodiment, the method involves selectively isolating anthocyanin-containing fractions from red cabbage extract to produce a natural anthocyanin-containing colorant providing color characteristics similar to those provided by synthetic FD&C Blue No. 1.

Selected anthocyanin-containing fractions of anthocyanin-containing fruit and vegetable juices and extracts may be isolated using an ion exchange column or semi-preparative HPLC column. Suitable ion exchange media include cation and anion exchange media. Suitable semi-preparative HPLC columns include C-18 columns. In an embodiment, the ion exchange column is activated with a solvent appropriate to the ion exchange media prior to loading of a vegetable or fruit juice or extract.

The anthocyanin-containing fraction is separated from the anthocyanin-containing vegetable or fruit juice or extract with a solvent at a pH of at least about 2, preferably at least about 4. In some embodiments, the anthocyanin fraction is separated with a solvent at a pH from about 2 to about 9. In yet another embodiment, the anthocyanin fraction is separated with a solvent at a pH from about 3 to about 9. In yet another embodiment, the anthocyanin fraction is separated with a solvent at a pH from about 4 to about 9. In yet another embodiment, the anthocyanin fraction is separated with a solvent at a pH from about 5 to about 9. In other embodiments, the anthocyanin fraction is separated with a solvent at a pH from about 6 to about 9. In still other embodiments, the anthocyanin fraction is separated with a solvent at a pH from about 7 to about 9.

Suitable solvents for eluting the selected anthocyanin-containing fractions include methanol, acetonitrile, water, and mixtures thereof, depending on the polarity of the column media and the solubility of the anthocyanin-containing juice or extract. In some embodiments, the solvent is an aqueous methanol solution.

Suitable agents that may be added to the solvent to adjust pH include potassium phosphate, sodium hydroxide, and the like.

In yet another embodiment, the invention is directed to a method of isolating a second fraction of anthocyanins from the anthocyanin-containing vegetable or fruit juice or extract, or a combination thereof, comprising: a) selectively separating anthocyanins on the ion exchange column based on differences in charge and polarity of the anthocyanin molecules using a second solvent of a select pH, wherein the pH value of the second solvent is different from, preferably higher than, the pH value of the solvent used to elute the first fraction; and b) selecting a second fraction or combination of fractions containing separated anthocyanins, such separated anthocyanins in the second fraction or the combination of fractions, when in an aqueous solution at pH of 8.0 provides color characteristics of those provided by FD&C Blue No. 1 as measured by having a maximum absorbance of 615 nm to 635 nm. In this embodiment, the first fraction, which may be separated with a first solvent of select pH, such as a solvent of pH of at least about 2, from the ion exchange column does not provide a mixture of separated anthocyanins that when in an aqueous solution at pH of 8.0 provides color characteristics of those provided by FD&C Blue No. 1 as measured by having a maximum absorbance of 615 nm to 635 nm. In an embodiment, the selected second anthocyanin-containing fraction is separated from the anthocyanin-containing vegetable or fruit juice or extract with a solvent at a pH from about 2 to about 9, or in one of the following ranges of increasing preference, i.e., about 3 to about 9, about 4 to about 9, about 5 to about 9, about 6 to about 9 or most preferably about 7 to about 9.

Additional anthocyanin-containing fractions may be isolated by further fractionating a selected anthocyanin-containing fraction using an ion exchange column or semi-preparative HPLC column. Suitable ion exchange media include cation and anion exchange media. Suitable semi-preparative HPLC columns include C-18 columns.

For example, in another embodiment, the fractionation method may further comprise the steps of: c) loading the selected one fraction or combination of fractions containing separated anthocyanins on an ion exchange column; d) selectively separating the anthocyanins loaded on the ion exchange column in step c) based on differences in charge and polarity of the anthocyanin molecules using a solvent of select pH; and e) selecting one fraction or a combination of fractions containing separated anthocyanins separated in step d) such that the separated anthocyanins selected in step e) when in an aqueous solution at pH of 8.0 provides a maximum absorbance of 620 nm to 635 nm. Third, fourth and further additional anthocyanin-containing fractions may be produced in a similar manner if desired. In yet another embodiment, the separated anthocyanins selected in step e) in at least one concentration in an aqueous solution at pH of 8.0 provides color characteristics having a ΔE value of 12 or less compared to the color characteristics defined by the segmented line defined by the L*a*b* values of 5 ppm and 10 ppm FD&C Blue No. 1 in aqueous solution.

In yet another embodiment, the step of selectively separating anthocyanins on the ion exchange column based on differences in charge and polarity of the anthocyanin molecules comprises the steps of (i) first using the solvent of select pH to obtain a first fraction and (ii) using a second solvent of second select pH, wherein the pH value of the second solvent is different from the pH value of the first solvent to obtain a subsequent fraction that is the one fraction or to obtain a combination of a plurality of subsequent fractions that is the combination of fractions, wherein the separated anthocyanins in the one fraction or combination of fractions when in at least one concentration in an aqueous solution at pH of 8.0 provides color characteristics having a ΔE value of 12 or less compared to the color characteristics defined by the segmented line defined by the L*a*b* values of 5 ppm and 10 ppm FD&C Blue No. 1 in aqueous solution.

In yet another embodiment, the step of selectively separating anthocyanins on the ion exchange column based on differences in charge and polarity of the anthocyanin molecules comprises the steps of (i) first using the solvent of select pH which is a first eluting solvent to obtain a first fraction and (ii) using one or more subsequent eluting solvents of select pH to obtain the one fraction or combination of fractions, wherein each eluting solvent is different, and the difference may be independently selected from the group of pH, solvent make-up and a combination thereof. Preferably the select pH of the first eluting solvent is lower than the select pH of the one or more subsequent fractions. Preferably the select pH will range from about 2 to about 9, or in one of the following ranges of increasing preference, i.e., about 3 to about 9, about 4 to about 9, about 5 to about 9, about 6 to about 9 or most preferably about 7 to about 9. In yet another embodiment, the separated anthocyanins in the one fraction or the combination of fractions, when at least one concentration is in an aqueous solution at pH of 8.0, provides color characteristics having a ΔE value of 12 or less compared to the color characteristics defined by the segmented line defined by the L*a*b* values of 5 ppm and 10 ppm FD&C Blue No. 1 in aqueous solution.

Isolated anthocyanin fractions may be used as colorants, or may be further processed by, for example, purification, concentration, deodorization, or color stabilization.

The selective separation method can be performed at a scale that produces commercially useful quantities of natural blue colorants.

The natural blue anthocyanin-containing colorants prepared by the method of this invention may be applied to or incorporated into all types of edible products, including foods for human and animal consumption, beverages, and pharmaceutical products. Examples of edible products include pet food and treats, dry goods (e.g., rice, grains, and cereals), soups and sauces, confectionery products (e.g., chocolates, sugar and sugarless candies of all types, chewing gum, candy bars, and sugar-coated confectionery), dessert products (e.g., pudding, frosting, icing, and toppings), baked goods (e.g., cakes, cookies, wafers, and biscuits), dairy products (e.g., yogurt, whipped cream, and cheese), beverages (e.g., dairy-based drinks, waters, juices, teas, and sodas), snack products (e.g., crackers, snack bars, pretzels, and chips), and pharmaceutical forms (e.g., tablets, suspensions, chewables, and syrups). The natural blue anthocyanin-containing colorant may also be incorporated into food grade colorant compositions, coatings, and inks. In an embodiment, the blue anthocyanin-containing colorant is included in a coating or ink applied to a surface of a confectionery product. In another embodiment, the blue anthocyanin-containing colorant is included in a coating or ink applied to a surface of a confectionery product, wherein the confectionery product is a confectionery center with a soft panned or hard panned sugar-based coating. In yet another embodiment, the blue anthocyanin-containing colorant is included in a coating or ink applied to a surface of a confectionery product, wherein the confectionery product is a confectionery center with a soft panned or hard panned sugarless coating.

In an embodiment, a red cabbage extract solution is fractionated using a strong cation exchange column. A first fraction is eluted with 75% v/v 0.1 M potassium phosphate buffer at pH 8 and 25% v/v methanol. A second fraction is eluted with 30% v/v 0.1 M potassium phosphate buffer at pH 8 and 70% v/v methanol.

In another embodiment, a red cabbage extract solution is fractionated using a strong cation exchange column. A first fraction is eluted with 75% v/v 0.1 M potassium phosphate buffer at pH 6 and 25% v/v methanol. A second fraction is eluted with 75% v/v 0.1 M potassium phosphate buffer at pH 7 and 25% v/v methanol. A third fraction is eluted with 75% v/v 0.1 M potassium phosphate buffer at pH 8 and 25% v/v methanol. A fourth fraction is eluted with 30% v/v 0.1 M potassium phosphate buffer at pH 8 and 70% v/v methanol.

In another embodiment, a red cabbage extract solution is separated using a C-18 semi-preparative HPLC column.

The method of selectively separating anthocyanin fractions from complex mixtures of anthocyanins in vegetable and fruit juices and extracts based on differences in charge and polarity of the anthocyanin molecules yields colorants providing color characteristics that are different from those provided by the complex mixtures.

This method of selectively separating anthocyanin fractions from complex mixtures of anthocyanins based on differences in polarity of the anthocyanin molecules fulfills the long-felt need for a means of obtaining natural colorants providing color characteristics similar to those provided by the synthetic colorant, FD&C Blue No. 1.

Specific embodiments of the invention will now be demonstrated by reference to the following examples. It should be understood that these examples are disclosed solely by way of illustrating the invention and variations within the spirit of the invention are anticipated.

EXAMPLE 1

Fractionation of Red Cabbage Extract Using Strong Cation Exchange Cartridge

An SCX (Strong Cation Exchange) solid phase extraction cartridge from Phenomenex® (Torrance, Calif.) was activated using pure methanol. The cartridge was washed using 0.01% v/v acidified water. An aqueous solution of red cabbage extract was loaded into the cartridge and washed with 0.01% v/v acidified water. A potassium phosphate buffer (0.1 M) at pH 8 was passed through the cartridge. Fraction 1 was eluted and collected using a 25% v/v methanol solution at pH 8. Fraction 2 was eluted and collected using a 70% v/v methanol solution at pH 8.

Fractions 1 and 2 were acidified with 2-5 ml of 88% v/v formic acid. The methanol was removed using a rotary evaporator.

In order to remove any salts, Fraction 1 was loaded into a C-18 cartridge and eluted with 0.01% v/v acidified water. The eluent was collected in 0.01% v/v acidified water, and the residual methanol was evaporated. Fraction 2 was also passed through a C-18 cartridge using the same procedure outlined for Fraction 1.

The maximum UV/VIS wavelength absorbance and color characteristics provided by the red cabbage extract solution (RCE) and Fractions 1 and 2 were analyzed at different pH values as shown below in Table 4.

TABLE 4

| pH | | $\lambda_{max}$ | L* | a* | b* | C* | h° |
|---|---|---|---|---|---|---|---|
| 6.0 | RCE | 552.80 | 93.86 | 2.48 | -2.73 | 3.69 | 312.31 |
| | Fraction 1 | 551.40 | 94.43 | 2.24 | -2.24 | 3.17 | 314.98 |
| | Fraction 2 | 553.60 | 93.63 | 2.64 | -3.29 | 4.22 | 308.79 |
| 6.6 | RCE | 560.80 | 92.86 | 1.74 | -3.89 | 4.27 | 249.07 |
| | Fraction 1 | 558.20 | 93.54 | 1.75 | -3.31 | 3.75 | 297.89 |
| | Fraction 2 | 565.60 | 92.62 | 1.59 | -4.46 | 4.73 | 289.62 |
| 7.0 | RCE | 596.80 | 92.65 | -0.49 | -4.10 | 4.13 | 263.14 |
| | Fraction 1 | 594.0 | 92.43 | -0.22 | -4.60 | 4.61 | 267.28 |
| | Fraction 2 | 599.80 | 92.07 | -1.17 | -5.11 | 5.24 | 257.10 |
| 7.6 | RCE | 612.0 | 92.10 | -3.23 | -4.62 | 5.64 | 235.00 |
| | Fraction 1 | 608.40 | 91.41 | -3.47 | -5.80 | 6.76 | 239.08 |
| | Fraction 2 | 616.40 | 91.62 | -4.17 | -5.68 | 7.05 | 233.67 |
| 8.0 | RCE | 612.40 | 91.17 | -5.05 | -5.77 | 7.67 | 228.82 |
| | Fraction 1 | 610.60 | 90.90 | -5.26 | -6.40 | 8.29 | 230.59 |
| | Fraction 2 | 619.40 | 91.56 | -5.80 | -5.81 | 8.21 | 225.04 |

Fraction 2 at pH 7.6 and pH 8.0 provided $\lambda_{max}$ values closest to that of synthetic FD&C Blue No. 1 ($\lambda_{max}$=630 nm), i.e., $\lambda_{max}$ values of 616.40 and 619.40, respectively.

ΔE values may also be calculated to compare the color characteristics provided by Fraction 2 at pH 7.6 and pH 8.0 to those provided by synthetic FD&C Blue No. 1. The ΔE values are equivalent to the minimum distances between the Fraction 2 color points in L*a*b* color space and the FD&C Blue No. 1 model. Therefore, Equation 5 is used to calculate the $d_{min}$, or ΔE, values from the following data:
The $X_0$ for Fraction 2 at pH 7.6 in L*a*b* color space is:
  $X_0$=(91.62, -4.17, -5.68)
The $X_0$ for Fraction 2 at pH 8.0 in L*a*b* color space is:
  $X_0$=(91.56, -5.80, -5.81)
$X_1$ and $X_2$ are two points from the FD&C Blue No. 1 model:
  $X_1$=(90.65, -24.40, -14.28)
  $X_2$=(97.69, -6.43, -3.57)
The calculated $d_{min}$, or ΔE, values are 6.7 for Fraction 2 at pH 7.6, and 6.0 for Fraction 2 at pH 8.0.

Figure 6:
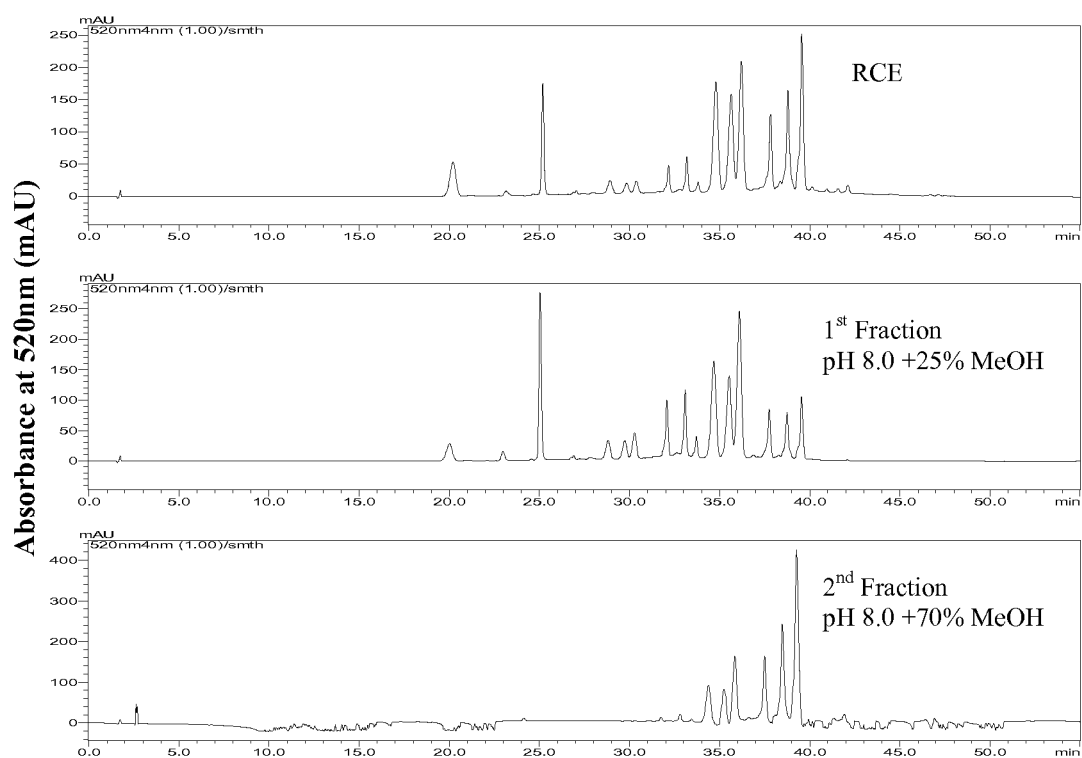
FIG. 6 shows HPLC chromatograms at 520 nm detection of red cabbage extract solution and two fractions isolated from red cabbage extract solution using a strong cation exchange column.

FIG. 6 provides HPLC chromatograms at 520 nm of the red cabbage extract solution (RCE) and Fractions 1 and 2. FIG. 6 shows that Fraction 2 has a higher concentration of the later-eluting peaks from the red cabbage extract solution.

EXAMPLE 2

Fractionation of Red Cabbage Extract Using Strong Cation Exchange Cartridge and Solvents of Different High pH Values An SCX (Strong Cation Exchange) solid phase extraction cartridge from Phenomenex® (Torrance, Calif.) was used. A red cabbage extract diluted in 0.01% v/v acidified water (10-15 ml) was loaded into the cartridge and washed with 0.01% v/v acidified water. A potassium phosphate buffer (0.1 M) at pH 6 was passed through the cartridge. Fraction 1 was eluted and collected using a 25% v/v methanol solution at pH 6. A potassium phosphate buffer (0.1 M) at pH 7 was passed through the cartridge. Fraction 2 was eluted and collected using a 25% v/v methanol solution at pH 7. A potassium phosphate buffer (0.1 M) at pH 8 was passed through the cartridge. Fraction 3 was eluted and collected using a 25% v/v methanol solution at pH 8. Fraction 4 was eluted and collected using a 70% v/v methanol solution at pH 8.

Fractions 1 to 4 were acidified with 20% v/v formic acid. The methanol was removed using a rotary evaporator.

In order to wash the salts, Fraction 1 was loaded into a C-18 cartridge and eluted with 0.01% v/v acidified water. The eluent was collected in 0.01% v/v acidified water, and the residual methanol was evaporated. Fractions 2 to 4 were also passed through a C-18 cartridge using the same procedure outlined for Fraction 1.

The maximum UV/VIS wavelength absorbance and color characteristics provided by the red cabbage extract solution (RCE) and Fractions 1 to 4 were analyzed at different pH values as shown below in Table 5.

TABLE 5

| pH | | $\lambda_{max}$ | L* | a* | b* | C* | h° |
|---|---|---|---|---|---|---|---|
| 6.0 | RCE | 553.0 | 93.08 | 3.10 | -3.52 | 4.69 | 311.40 |
| | Fraction 1 | 549.8 | 95.21 | 1.64 | -1.33 | 2.11 | 320.92 |
| | Fraction 2 | 552.4 | 94.75 | 1.99 | -1.96 | 2.79 | 315.53 |
| | Fraction 3 | 552.0 | 94.42 | 2.19 | -2.25 | 3.13 | 314.20 |
| | Fraction 4 | 554.2 | 92.41 | 3.49 | -4.46 | 5.66 | 307.99 |
| 7.0 | RCE | 596.0 | 91.07 | -0.77 | -5.72 | 5.77 | 262.31 |
| | Fraction 1 | 592.6 | 93.37 | -0.12 | -3.36 | 3.36 | 267.91 |
| | Fraction 2 | 591.6 | 92.59 | 0.19 | -4.35 | 4.36 | 272.54 |
| | Fraction 3 | 594.4 | 92.32 | -0.38 | -4.62 | 4.63 | 265.34 |
| | Fraction 4 | 601.8 | 90.65 | -1.96 | -6.52 | 6.81 | 253.30 |
| 8.0 | RCE | 612.6 | 90.00 | -6.20 | -6.84 | 9.23 | 227.77 |
| | Fraction 1 | 606.6 | 91.05 | -4.44 | -5.87 | 7.36 | 232.93 |
| | Fraction 2 | 608.8 | 90.28 | -5.40 | -7.14 | 8.95 | 232.86 |
| | Fraction 3 | 611.6 | 90.21 | -5.92 | -7.16 | 9.29 | 230.42 |
| | Fraction 4 | 622.2 | 90.08 | -7.87 | -7.20 | 10.67 | 222.43 |

Fraction 4 at pH 8.0 provided a $\lambda_{max}$ value closest to that of synthetic FD&C Blue No. 1 ($\lambda_{max}$=630 nm), i.e., a $\lambda_{max}$ value of 622.2.

A ΔE value may also be calculated to compare the color characteristics provided by Fraction 4 at pH 8.0 to those provided by synthetic FD&C Blue No. 1. The ΔE value is equivalent to the minimum distance between the Fraction 4 color point in L*a*b* color space and the FD&C Blue No. 1 model. Therefore, Equation 5 is used to calculate the $d_{min}$, or ΔE, value from the following data:
The $X_0$ for Fraction 4 at pH 8.0 in L*a*b* color space is:
  $X_0$=(90.08, -7.87, -7.20)
$X_1$ and $X_2$ are two points from the FD&C Blue No. 1 model:
  $X_1$=(90.65, -24.40, -14.28)
  $X_2$=(97.69, -6.43, -3.57)
The calculated $d_{min}$, or ΔE, value is 6.7 for Fraction 4 at pH 8.0.

Figure 7:
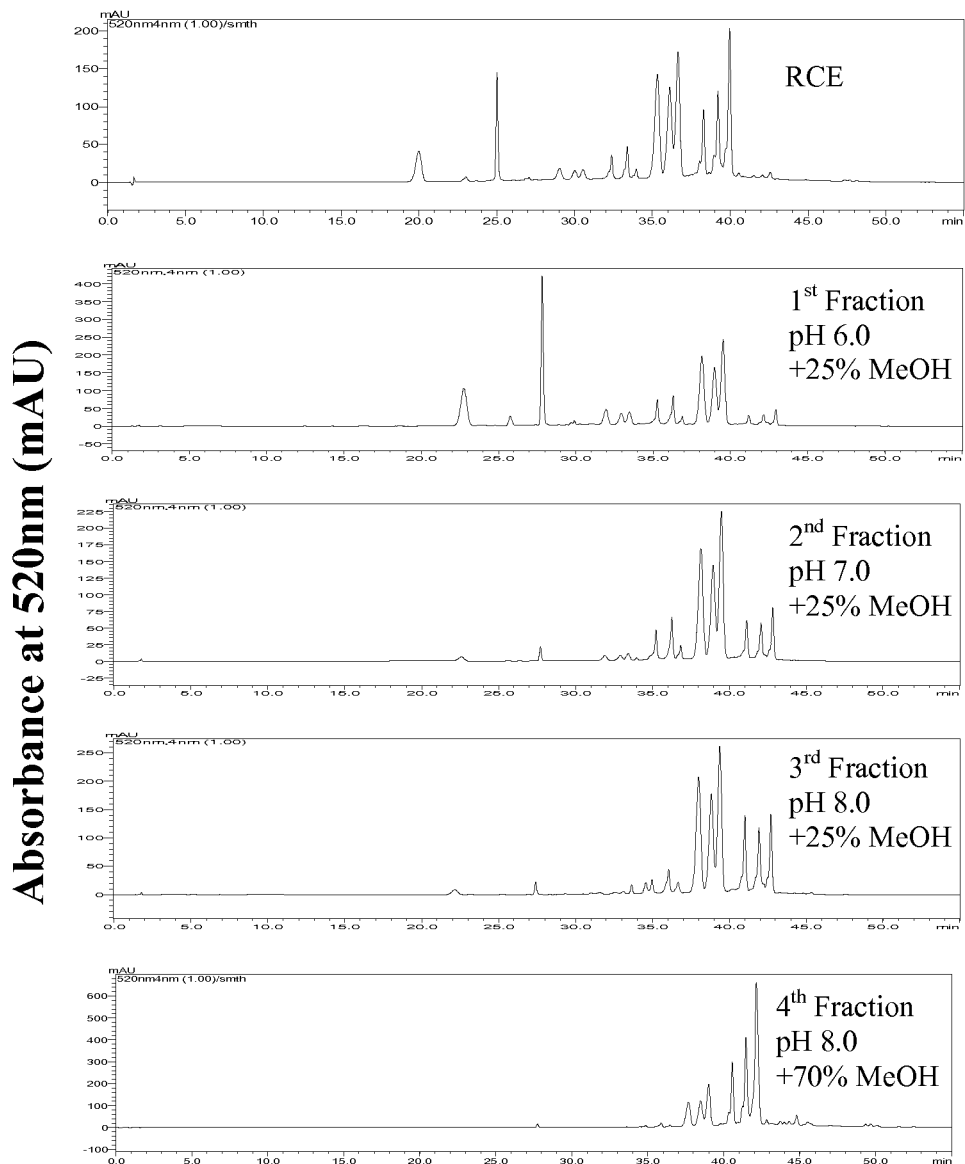
FIG. 7 shows HPLC chromatograms at 520 nm detection of red cabbage extract solution and four fractions isolated from red cabbage extract solution using a strong cation exchange column.
Figure 8:
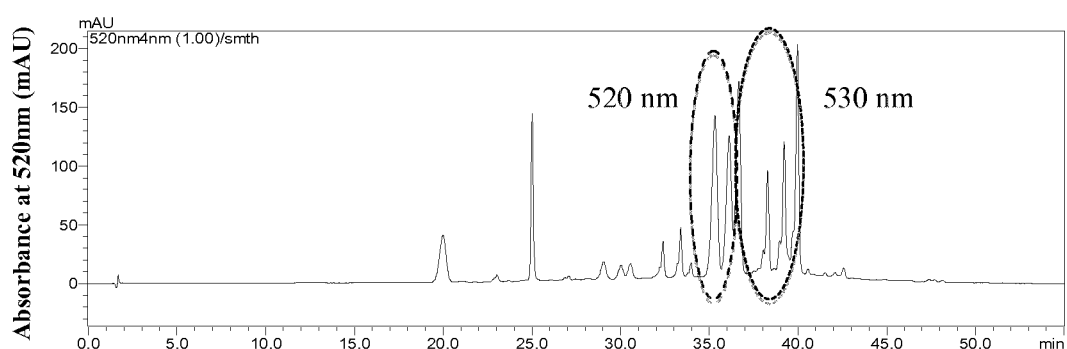
FIG. 8 shows HPLC chromatograms at 520 nm detection of red cabbage extract solution identifying two groups of peaks that were targeted for isolating. These two groups of peaks were isolated as the "520-nm Fraction" and the "530-nm Fraction."

FIG. 7 provides the HPLC chromatograms at 520 nm detection of the red cabbage extract solution (RCE) and Fractions 1 to 4. FIG. 7 shows that Fraction 4 has a higher concentration of the later-eluting peaks from the red cabbage extract solution.

EXAMPLE 3

Separation of Red Cabbage Extract Peak Groups Using Semi-Preparative HPLC

Fractions associated with two specific groups of peaks, as shown in the chromatogram of FIG. 7, may be separated and collected from red cabbage extract solution using semi-preparative HPLC. The red cabbage extract solution was loaded onto a C-18 semi-preparative HPLC cartridge and two fractions, the 520-nm Fraction ($\lambda_{max}$=524 nm) and the 530-nm Fraction ($\lambda_{max}$=532 nm), were eluted using an acidic acetonitrile and water gradient. The residual acetonitrile was evaporated from each fraction with a rotary evaporator.

Color characterization was performed after adjusting the concentrations of the fractions and mixing separate fraction aliquots with buffer to produce five aliquots at pH 6, 6.6, 7, 7.6, and 8. The maximum UV/VIS wavelength absorbance and color characteristics of the 520-nm and 530-nm Fraction aliquots were analyzed, and the results are provided in Table 6.

TABLE 6

| Fraction | pH | $\lambda_{max}$ | Abs (Amu) | L* | a* | b* | C* | h° |
|---|---|---|---|---|---|---|---|---|
| 520-nm | 1-2 | 524 | 2.161 | 80.05 | 33.41 | -6.17 | 33.97 | 349.54 |
| (107.71 | 6.0 | ND[1] | ND | 95.95 | 0.95 | -0.72 | 1.19 | 322.87 |
| mg/L) | 6.6 | ND | ND | 95.64 | 0.80 | -1.08 | 1.34 | 306.49 |
|  | 7.0 | 585.80 | 0.2 | 99.32 | 0.48 | -2.56 | 2.60 | 280.71 |
|  | 7.6 | 602.00 | 0.389 | 92.56 | -1.72 | -4.70 | 5.01 | 249.91 |
|  | 8.0 | 603.80 | 0.488 | 92.09 | -3.15 | -5.17 | 6.06 | 238.68 |
| 530-nm | 1-2 | 538 | 0.752 | 89.83 | 13.86 | -5.80 | 15.02 | 337.31 |
| (55.60 | 6.0 | 554.40 | 0.610 | 89.27 | 6.07 | -8.06 | 10.10 | 306.98 |
| mg/L) | 6.6 | 587.00 | 0.707 | 87.64 | 1.43 | -9.96 | 10.06 | 278.14 |
|  | 7.0 | 599.60 | 0.848 | 86.88 | -2.85 | -10.96 | 11.33 | 255.45 |
|  | 7.6 | 621.80 | 1.156 | 87.67 | -5.44 | -9.90 | 11.30 | 241.23 |
|  | 8.0 | 621.00 | 1.294 | 86.39 | -11.79 | -11.98 | 16.81 | 225.45 |

[1]ND indicates that the absorbance spectra of the sample did not show a maximum peak in the visible range.

The 530-nm Fraction has a maximum absorbance of about 621 nm at pH 7.6 and pH 8.0 and provides a $\lambda_{max}$ closest to that of synthetic FD&C Blue No. 1 ($\lambda_{max}$=630 nm).

ΔE values may also be calculated to compare the color characteristics provided by the 530-nm Fraction at pH 7.6 and pH 8.0 to those provided by synthetic FD&C Blue No. 1. The ΔE values are equivalent to the minimum distances between the 530-nm Fraction color points in L*a*b* color space and the FD&C Blue No. 1 model. Therefore, Equation 5 is used to calculate the $d_{min}$, or ΔE, values from the following data:

The $X_0$ for the 530-nm Fraction at pH 7.6 in L*a*b* color space is:

$X_0$=(87.67, -5.44, -9.90)

The $X_0$ for the 530-nm Fraction at pH 8.0 in L*a*b* color space is:

$X_0$=(86.39, -11.79, -11.98)

$X_1$ and $X_2$ are two points from the FD&C Blue No. 1 model:

$X_1$=(84.25, -37.23, -23.42)

$X_2$=(90.65, -24.40, -14.28)

The calculated $d_{min}$, or ΔE, values are 12.1 for the 530-nm Fraction at pH 7.6, and 9.9 for the 530-nm Fraction at pH 8.0.

Figure 9:
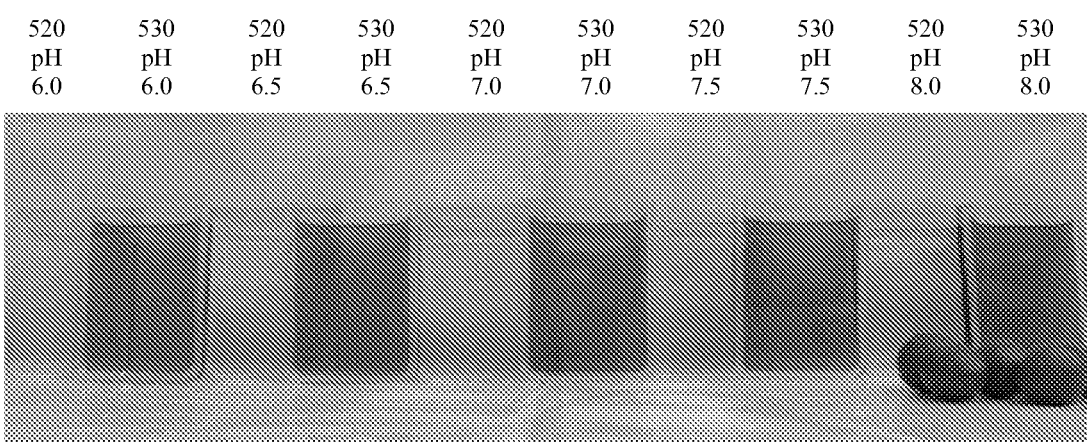
FIG. 9 provides a visual comparison of the colors provided by the 520-nm and 530-nm Fractions at different pH values.

FIG. 9 provides a visual comparison of the 520-nm and 530-nm Fractions at different pH values. The concentration of the 520-nm Fraction is 107.7 mg/L (Cyn-3-glu) and the concentration of the 530-nm Fraction is 55.6 mg/L (Cyn-3-glu). At neutral and higher pH, it can be seen that the 530-nm Fraction provides two to four times the chroma (as measured by C*) of the 520-nm Fraction at half the colorant concentration.

Figure 10:
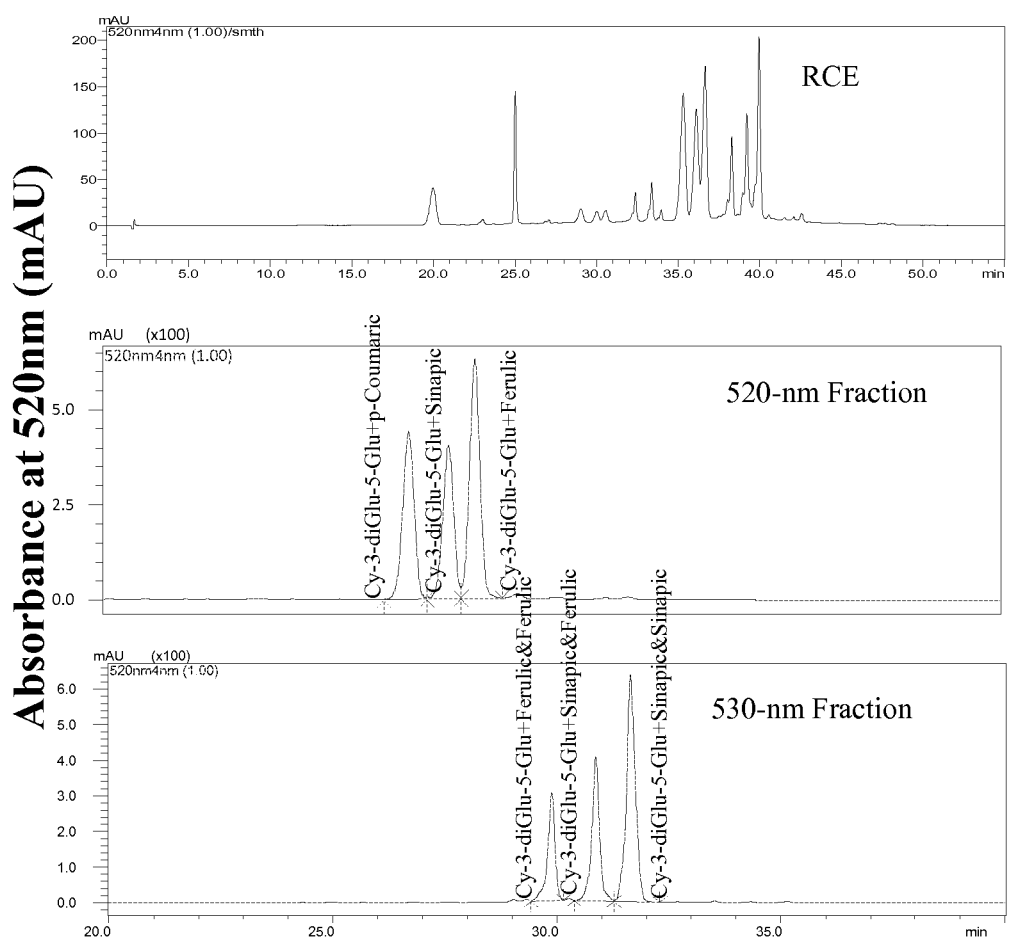
FIG. 10 shows HPLC chromatograms at 520 nm detection of red cabbage extract solution and two fractions isolated from red cabbage extract solution using semi-preparative HPLC.

FIG. 10 provides the HPLC chromatograms at 520 nm detection of the red cabbage extract solution and the 520-nm and 530-nm Fractions. FIG. 10 indicates that each fraction contains three distinct anthocyanin compounds.

COMPARATIVE EXAMPLE

Several different concentrations of the red cabbage anthocyanin solution disclosed in the Examples of WO 2004/012526 were prepared at pH of 8.0. There was no fractionation conducted to separate and collect separated anthocyanin-containing colorants. The maximum absorbance of the resulting solutions was 610 nm. The color was not considered an acceptable match for the color of FD&C Blue No. 1.

What is claimed:

1. A method of isolating a fraction of anthocyanins from an anthocyanin-containing vegetable or fruit juice or extract, or a combination thereof, comprising:
    a) loading an anthocyanin-containing vegetable or fruit juice or extract, or a combination thereof, on an ion exchange column;
    b) selectively separating anthocyanins into two or more fractions on the ion exchange column based on differences in charge and polarity of the anthocyanin molecules using a solvent of select pH, wherein the pH is from 4 to 9;
    c) selecting one fraction or a combination of fractions containing separated anthocyanins, such that the separated anthocyanins in the one fraction or the combination of fractions, when in an aqueous solution at pH 8.0 has a maximum absorbance of 615 nm to 635 nm; and
    d) adjusting a pH of the one fraction or the combination of fractions to obtain a solution comprising separated anthocyanins having a maximum absorbance of 615 nm to 635 nm.

2. The method of claim 1, wherein the separated anthocyanins in the one fraction or the combination of fractions in at least one concentration in an aqueous solution at pH of 8.0 provides color characteristics having a ΔE value of 12 or less compared to the color characteristics defined by the segmented line defined by the L*a*b* values of 5 ppm and 10 ppm FD&C Blue No. 1 in aqueous solution.

3. The method of claim 1, wherein the source of the anthocyanin-containing vegetable or fruit juice or extract is selected from the group consisting of red cabbage, purple sweet potato, blue potato, black carrot, purple carrot and combinations thereof.

4. The method of claim 3, wherein the source of the anthocyanin-containing vegetable or fruit juice or extract is red cabbage.

5. The method of claim 1, wherein a first anthocyanin-containing fraction is eluted with a 25% v/v methanol solution at pH 8 and a subsequent anthocyanin-containing fraction that is the one fraction or a plurality of subsequent fractions that is the combination of fractions is eluted with a 70% v/v methanol solution at pH 8.

6. The method of claim 5, further comprising a step of purifying the one fraction or the combination of fractions.

7. The method of claim 6, wherein the separated anthocyanins of the one fraction or the combination of fractions in at least one concentration in an aqueous solution at pH of 8.0 provides color characteristics having a $\Delta E$ value of 12 or less compared to the color characteristics defined by the segmented line defined by the L*a*b* values of 5 ppm and 10 ppm FD&C Blue No. 1 in aqueous solution.

8. The method of claim 1, wherein the ion exchange column is a cation exchange column.

9. The method of claim 1, wherein the step of selectively separating anthocyanins on the ion exchange column based on differences in charge and polarity of the anthocyanin molecules comprises the steps of (i) first using the solvent of select pH to obtain a first fraction and (ii) using a second solvent of a second select pH, wherein the pH value of the second solvent is different from the pH value of the first solvent to obtain a subsequent fraction that is the one fraction or to obtain a combination of a plurality of subsequent fractions that is the combination of fractions, wherein the separated anthocyanins in the one fraction or combination of fractions when in at least one concentration in an aqueous solution at pH of 8.0 provides color characteristics having a $\Delta E$ value of 12 or less compared to the color characteristics defined by the segmented line defined by the L*a*b* values of 5 ppm and 10 ppm FD&C Blue No. 1 in aqueous solution.

10. The method of claim 1, further comprising the steps of:
  e) loading the selected one fraction or combination of fractions containing separated anthocyanins on an ion exchange column;
  f) selectively separating the anthocyanins loaded on the ion exchange column in step e) based on differences in charge and polarity of the anthocyanin molecules using a solvent of select pH; and
  g) selecting one fraction or a combination of fractions containing separated anthocyanins separated in step f) such that the separated anthocyanins selected in step g) when in an aqueous solution at a pH of 8.0 provides a maximum absorbance of 620 nm to 635 nm.

11. The method of claim 10, wherein the separated anthocyanins selected in step f) in at least one concentration in an aqueous solution at pH of 8.0 provides color characteristics having a $\Delta E$ value of 12 or less compared to the color characteristics defined by the segmented line defined by the L*a*b* values of 5 ppm and 10 ppm FD&C Blue No. 1 in aqueous solution.

12. The method of claim 1, wherein the step of selectively separating anthocyanins on the ion exchange column based on differences in charge and polarity of the anthocyanin molecules comprises the steps of (i) first using the solvent of select pH which is a first eluting solvent to obtain a first fraction and (ii) using one or more subsequent eluting solvents of select pH to obtain the one fraction or combination of fractions, wherein each eluting solvent is different, and the difference may be independently selected from the group of pH, solvent makeup and a combination thereof.

13. The method of claim 12, wherein the separated anthocyanins in the one fraction or the combination of fractions, when in at least one concentration in an aqueous solution at pH of 8.0 provides color characteristics having a $\Delta E$ value of 12 or less compared to the color characteristics defined by the segmented line defined by the L*a*b* values of 5 ppm and 10 ppm FD&C Blue No. 1 in aqueous solution.

14. The method of claim 13, wherein the first eluting solvent is a mixture of an organic solvent and water at a first concentration of organic solvent and a subsequent eluting solvent is used that is a second mixture of an organic solvent and water having a second concentration of organic solvent, wherein the first concentration is different than the second concentration.

15. The method of claim 12, wherein the first eluting solvent has a select pH that is different than a select pH of the subsequent eluting solvent.

16. The method of claim 15, wherein the select pH of the first eluting solvent is lower than the select pH of the subsequent eluting solvent.

* * * * *